US00PP33657P3

(12) United States Plant Patent
Jennings

(10) Patent No.: US PP33,657 P3
(45) Date of Patent: Nov. 23, 2021

(54) ***RUBUS* PLANT NAMED 'GLEN MOR'**

(50) Latin Name: *Rubus idaeus*
Varietal Denomination: Glen Mor

(71) Applicant: James Hutton Ltd., Dundee (GB)

(72) Inventor: Sophia N Jennings, Dundee (GB)

(73) Assignee: JAMES HUTTON LTD., Dundee (GB)

( * ) Notice: Subject to any disclaimer, the term of this patent is extended or adjusted under 35 U.S.C. 154(b) by 0 days.

(21) Appl. No.: 17/035,414

(22) Filed: Sep. 28, 2020

(65) Prior Publication Data

US 2021/0105923 P1 Apr. 8, 2021

(30) Foreign Application Priority Data

Oct. 8, 2019 (QZ) ..... PBR 2019/2569

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499
See application file for complete search history.

(56) References Cited

PUBLICATIONS

"Glen Mor; the new raspberry that gives more", source James Hutton, https://www.huttonltd.com/news/glen-mor-new-raspberry-gives-more, published Jul. 10, 2020 downloaded from https://www.hortidaily.com/article/9233296/glen-mor-the-new-raspberry-that-gives-more/.*

* cited by examiner

*Primary Examiner* — Anne Marie Grunberg
(74) *Attorney, Agent, or Firm* — Penny J. Aguirre

(57) ABSTRACT

A new cultivar of *Rubus* plant named 'Glen Mor' that is characterized by its spineless canes, its resistance to *Phytophthora* root rot, its pink petioles on actively growing vegetative canes, its early summer fruit production on floricanes, its early summer fruit production on floricanes, its late fruit laterals low on the floricane during the summer allowing a longer fruit season, and its tip fruit in autumn on the top 6 to 10 buds on the primocane.

2 Drawing Sheets

Botanical classification: *Rubus idaeus.*
Cultivar designation: 'Glen Mor'.

CROSS-REFERENCE TO A RELATED APPLICATION

This application claims priority to European Community Plant Variety Office (CPVO) Plant Breeder's Rights Application No. 2019/2569 filed on Oct. 8, 2019, under 35 U.S.C. 119(f), the entire contents of which is incorporated by reference herein.

BACKGROUND OF THE INVENTION

The present invention relates to a new and distinct cultivar of *Rubus idaeus* named 'Glen Mor' and will be referred to hereinafter by its cultivar name, 'Glen Mor'. 'Glen Mor' is a new raspberry plant grown for fruit production.

The new cultivar was derived from a controlled breeding program in Dundee, Scotland, United Kingdom. The objectives of the breeding program are to develop new raspberry cultivars suitable for the fresh fruit market, both floricane and primocane, with high fruit quality, improved agronomic qualities and increased tolerance to pathogens.

The Inventor made a cross in spring of 2009 between an unnamed proprietary plant in the Inventor's breeding program, reference no. 0304F6, as the female parent and *Rubus idaeus* 'Autumn Treasure' (U.S. Plant Pat. No. 20,769) as the male parent. The Inventor selected 'Glen Mor' in 2011 as a single unique plant amongst the seedlings that resulted from the above cross.

Asexual propagation of the new cultivar was first accomplished by the Inventor by root cuttings in Dundee, Scotland, United Kingdom in 2011. Asexual propagation by root cuttings and tissue culture using meristematic tissue has shown that the unique features of the new cultivar are stable and reproduced true to type in successive generations.

SUMMARY OF THE INVENTION

The following traits have been repeatedly observed and represent the characteristics of the new cultivar. These attributes in combination distinguish 'Glen Mor' as a new and unique cultivar of *Rubus*.

1. 'Glen Mor' exhibits spineless canes.
2. 'Glen Mor' exhibits resistance to *Phytophthora* root rot.
3. 'Glen Mor' exhibits pink petioles on actively growing vegetative canes.
4. 'Glen Mor' exhibits early summer fruit production on floricanes.
5. 'Glen Mor' exhibits late fruit laterals low on the floricane during the summer allowing a longer fruit season.
6. 'Glen Mor' exhibits tip fruit in autumn on the top 6 to 10 buds on the primocane.

The seed parent of 'Glen Mor' differs from 'Glen Mor' in being a true floricane producer, having a high chill requirement to produce flowers, fruit that is softer, and in being susceptible to *Phytophthora* root rot. The pollen parent of 'Glen Mor' differs from 'Glen Mor' in being a true primocane producer and having fruit that is smaller in size and long conical in shape. 'Glen Mor' can be compared to the *Rubus* cultivars 'Tulameen' (not patented) and 'Glen Ample' (U.S. Plant Pat. No. 11,418). 'Tulameen' and 'Glen Ample' are both similar to 'Glen Mor' in fruiting in summer on floricanes. 'Tulameen' differs from 'Glen Mor' in having canes with spines, fruit that is softer, later fruit cropping in the summer and in being very susceptible to *Phytophthora* root rot. 'Glen Ample' differs from 'Glen Mor' in having fruit that commences cropping later in the season, less fruit that are rounder in shape with larger druplets, and in in lacking tip fruit production in autumn.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website and facebook listings by James Hutton Ltd.

BRIEF DESCRIPTION OF THE DRAWINGS

The accompanying colored photographs illustrate the overall appearance and distinct characteristics of the new *Rubus*. The photographs were taken of a plant 24 months in age as grown in a polytunnel in a 10-liter container in Dundee, Scotland, United Kingdom.

The photograph in FIG. 1 provides a view of immature and mature fruit 'Glen Mor'.

Figure 1:
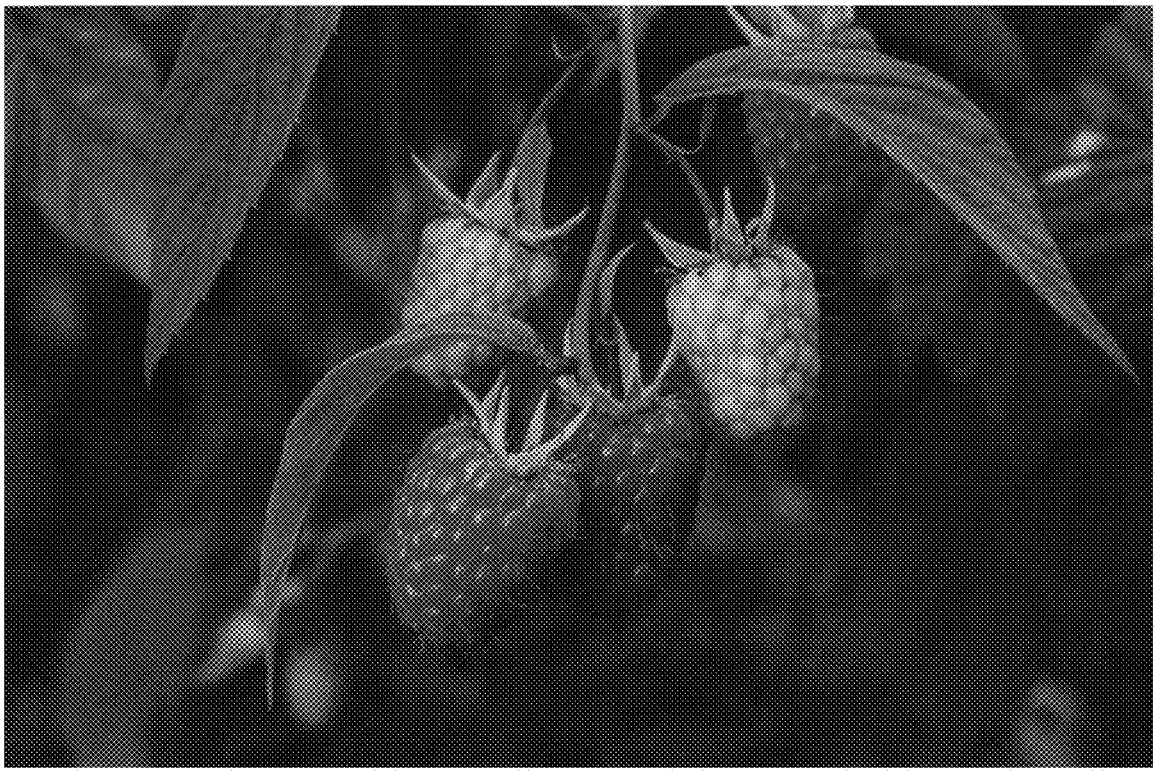
Figure 2:
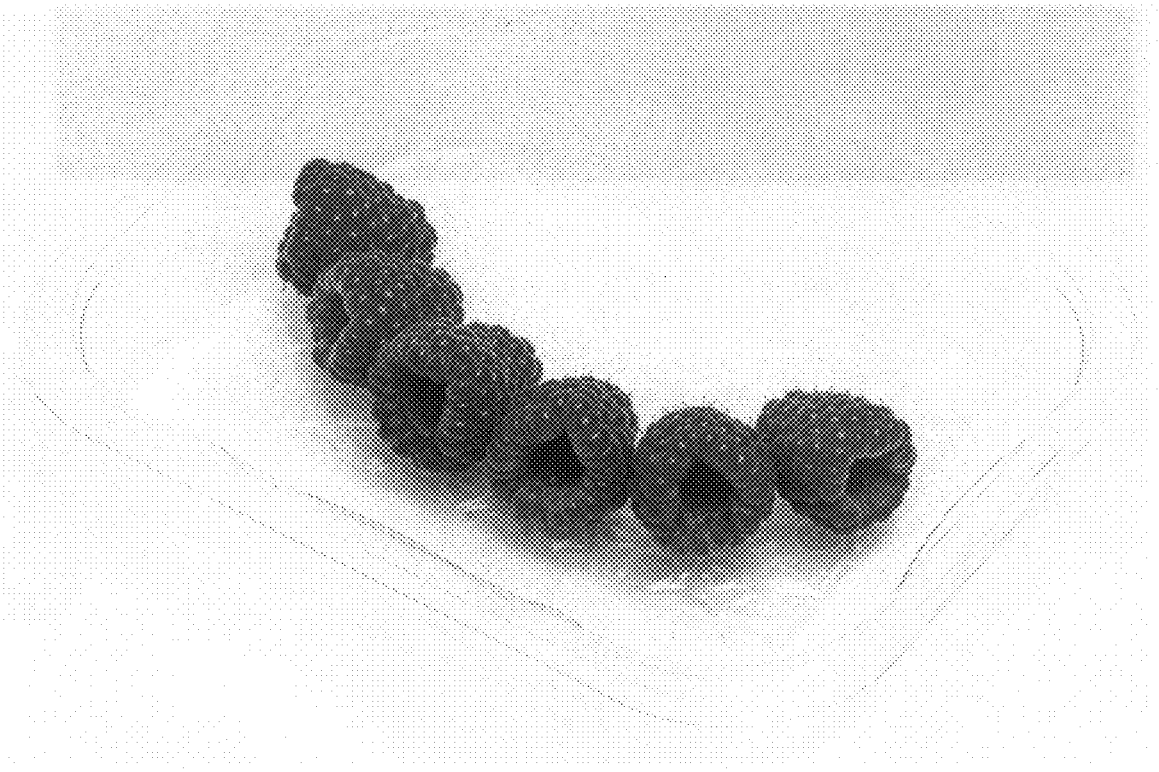

The photograph in FIG. 2 provides a close-up view of harvested fruit of 'Glen Mor'.

The colors in the photographs are as close as possible with the photographic and printing technology utilized. The colors in the photographs may differ slightly from the color values cited in the detailed botanical description, which accurately describe the colors of the new *Rubus*.

DETAILED BOTANICAL DESCRIPTION OF THE PLANT

The following is a detailed description of plants 24 months in age as grown in a polytunnel in 10-liter containers in Dundee, Scotland, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Fruit producing perennial, hybrid between two fruiting habits (floricane x primocane), grown primarily for floricane production.

*Plant habit*.—Upright.

*Height and spread*.—An average of 1.85 m in height and 22 cm in spread as grown in a 10-liter container.

*Hardiness*.—This trait has not been fully characterized in a range of cold weather climates, but the plants can successfully grow in western Europe (U.K. Hardiness Zone 7).

*Diseases and pests*.—Resistance to root rot (caused by *Phytophthora fragariae* var. *rubi*) and large raspberry aphid (caused by *Amphorophora idaei*).

*Root description*.—Demonstrates high root vigor.

*Branching habit*.—Un-branched.

*Propagation*.—Root cuttings or tissue culture.

*Root development*.—An average of 2 weeks to initiate roots, an average of 6 months to fully develop as a plant with 3 canes that are an average of 2 m in height.

*Growth rate*.—Moderate to vigorous cane growth, prolific spawn production.

Cane description:

*Cane size*.—An average of 1.8 m in length and an average of 8 mm in width.

*Cane internode length*.—Average of 7.5 cm.

*Cane shape and aspect*.—Angled.

*Cane strength*.—Strong.

*Cane color*.—New canes; 144A to 144B and heavily suffused with 186C, mature canes; 175A, internodes 175A.

*Stem surface*.—Glabrous and spine free.

*Stipules*.—2 per petiole, leafy; narrowly elliptic in shape, an average of 7.8 mm in length and >1 mm in width, apex narrowly acute, base cuneate, upper and lower surface color 144A.

*Cane production*.—Crops primarily on the floricanes in spring and summer but produces tip fruit on top 6-10 buds on primocanes in the autumn, otherwise develops in spring and initiate flower buds in autumn that develop into the floricane the following season.

Foliage description:

*Time of vegetative bud burst*.—Very early season; about March 25th.

*Vegetative bud size*.—An average of 3.6 mm in length and 2.2 mm in width on current year's growth.

*Leaf shape*.—Ovate.

*Leaf arrangement*.—1 terminal and 1 to 2 lateral pairs.

*Leaf division*.—Compound, 1 to 3 leaflets.

*Leaf attachment*.—Petiolate.

*Leaf size*.—An average of 20 cm in length and 23 cm in width.

*Leaflet shape*.—Majority ovate, some lanceolate or epileptic.

*Leaflet base*.—Obtuse and Ovate.

*Leaflet apex*.—Acute.

*Leaflet venation*.—Pinnate.

*Leaflet margins*.—Serrate with mucronate tip on serrations.

*Leaflet arrangement*.—1 terminal and 1 to 2 lateral pairs.

*Leaflet attachment*.—Sessile on lateral leaflets, petiolate on terminal leaflets.

*Leaflet surface*.—Upper and lower surface rugose, not visibly pubescent under a handheld microscope.

*Leaflet color*.—Young; upper surface 137A, lower surface 138C, mature leaf; upper surface 141A, lower surface 144A, no change in autumn.

*Leaflet size*.—Terminal leaflet; an average of 10.9 cm in length and 6 cm in width.

*Petioles*.—Round in shape, an average of 9.1 cm in length and 3 mm in width, young growth; 186C on both surfaces, mature growth; upper surface color 144A, lower surface color 186C.

*Relative position of lateral leaflet*.—Non-overlapping to slightly overlapping at base.

*Profile of leaflet cross-section*.—Slightly concave.

*Rachis*.—Round in shape, an average of 2.65 cm in length and 3 mm in width, upper surface color 181C, lower surface color 144A tinged with 181C.

Inflorescence description:

*Blooming period*.—Very early in the spring season, flowering for 6 to 8 weeks from mid-May into summer in Scotland.

*Inflorescence*.—Panicle, average of 26.2 cm in length on upper laterals and 35.6 cm in length on lower laterals.

*Peduncle*.—Oval in shape, an average of 8.8 mm in length and 1 mm in width, held straight to vertical stem, color of upper surface 59A, color of lower surface 144D, strong.

*Pedicels*.—Oval in shape, 181C in color, an average of 1.64 cm in length and 1 mm in width, glossy surface, strong, held in multiple angles between 10° to 90° to peduncle.

*Flower buds*.—Nearly orbicular in shape, average of 1.1 cm in length and 6 mm in diameter, color; immature sepal portion 144A with borders NN155D, petal portion 142D and NN155D, surface petal portion glabrous.

*Flower type*.—Spreading calyx with center of numerous stamens and with numerous pistols, petals quickly shed upon opening.

*Flower number*.—An average of 13 per inflorescence, 18 inflorescences per plant.

*Flower fragrance*.—None.

*Flower size*.—Average of 7.8 mm in height and 1.8 cm in diameter.

*Sepals*.—5, slightly curved, an average of 7 mm in length, 3.8 mm in width, broadly ovate to near deltoid in shape, base broadly cuneate, apex acute, entire margin, color when opening and mature; 144A on upper surface, 142D on lower surface.

*Petals*.—5, an average of 8 mm in length, 3 mm in width, base cuneate, apex obtuse, entire margin with medium undulation, glabrous and matte on upper and lower surfaces, color; when opening and fully open upper and lower surface NN155D.

*Bracts*.—Linear, obcordate and obovate at base of pedicel, leafy; narrowly elliptic in shape, an average of 10.6 cm in length, 1 cm in width, apex narrowly acute, cuneate base, entire margin, upper surface color 137B, lower surface 138C.

*Androecium*.—Stamens; an average of 85, filaments; 3 mm in length, NN155D in color, anthers; 1 mm in length, >1 mm in width, 11C in color, pollen; moderate in quantity.

*Gynoecium*.—Pistils; 120, average of 5 mm in length, stigmas; cup-shaped, >1 mm in length and diameter, 11C in color, style; 3 mm in length, 11C in color, ovary; 11C in color.

Fruit description:

*Fruit number*.—An average of 15 per lateral.

*Fruit size*.—An average of 3.6 cm in length and 2.5 cm in diameter.

*Fruit color*.—A blend of 53A and 53B.

*Fruit adherence to plug*.—Medium.

*Fruit glossiness*.—Moderate.

*Fruit firmness*.—Medium.

*Fruit shape*.—Broad conical.

*Fruit texture*.—Smooth, few hairs, glabrous except for persistent styles >3 mm in length and 47A in color.

*Druplets*.—An average of 98 per berry, 6.4 mm in length and width.

*Seed*.—Reniform in shape, average of 88 per fruit, 3.4 mm in length and 1 mm in width, 27D in color.

*Cropping frequency*.—Annually, on floricanes and tip fruit on primocanes.

*Harvest dates*.—Typically, first harvest date of June 25$^{th}$, last harvest date of August 18$^{th}$ when planted in a polytunnel in Dundee, Scotland, United Kingdom.

*Flavor*.—A good balance of sweet and acidic with hints of coconut.

*Fruit weight*.—5.9 g/fruit.

*Brix*.—9° to 10°.

*Titratable acidity*.—9.9%.

*Shelf life*.—An average of 7 to 10 days after picking.

*Market use*.—Fresh fruit.

It is claimed:

1. A new and distinct cultivar of *Rubus idaeus* plant named 'Glen Mor' as herein illustrated and described.

* * * * *